United States Patent [19]

Bailey et al.

[11] Patent Number: 4,898,880

[45] Date of Patent: Feb. 6, 1990

[54] N-(HETEROCYCLE)ALKYL)-1H-PYRAZOLE-1-ALKANAMIDES AS ANTIARRHYTHMIC AGENTS, COMPOSITIONS AND USE

[75] Inventors: Denis M. Bailey, East Greenbush; George Y. Lesher, Schodack; Thomas E. D'Ambra, North Greenbush, all of N.Y.

[73] Assignee: Sterling Drug Inc., New York, N.Y.

[21] Appl. No.: 327,218

[22] Filed: Mar. 22, 1989

[51] Int. Cl.$^4$ .................. A61K 31/415; C07D 403/12
[52] U.S. Cl. ..................................... 514/406; 514/252; 514/256; 514/326; 514/341; 514/397; 514/404; 544/333; 544/371; 544/405; 546/211; 546/279; 548/336; 548/364; 548/374
[58] Field of Search ...................... 544/333, 371, 405; 546/211, 279; 548/336, 364, 374; 514/252, 256, 326, 371, 397, 404, 406

[56] References Cited

U.S. PATENT DOCUMENTS 4,182,895 1/1980 Bailey .................................. 548/378

OTHER PUBLICATIONS

Ezrin et al. FASEB Journal 2, A1557 (1988).

Primary Examiner—Robert W. Ramsuer
Attorney, Agent, or Firm—Philip E. Hansen; Paul E. DuPont

[57] ABSTRACT

N-[(heterocycle)alkyl]-3,4 (or 4,5)-diaryl-1H-pyrazole-1-acetamides and pyrazole-1-propanamides, useful for treating cardiac arrhythmias in mammals, are prepared by reacting a lower-alkyl ester of pyrazole-1-acetic or propanoic acid with an appropriate (heterocycle-alkyl) amine or by reacting a pyrazole-1-acetic or propanoic acid with an appropriate (heterocycle-alkyl)amine.

16 Claims, No Drawings

N-(HETEROCYCLE)ALKYL)-1H-PYRAZOLE-1-ALKANAMIDES AS ANTIARRHYTHMIC AGENTS, COMPOSITIONS AND USE

BACKGROUND OF THE INVENTION

1. Field of the Invention

The present invention relates to novel N-[(heterocycle)alkyl]-3,4(or 4,5)-diaryl-1H-pyrazole-1-acetamides or propanamides, processes for the synthesis of said pyrazole-1-alkanamides, and methods for treating cardiac arrhythmia in mammals utilizing said pyrazole-1-alkanamides.

Information Disclosure Statement

U.S. Pat. No. 4,695,566 to Heinemann et.al. discloses as antiarrythmic agents 1H-pyrazol-3-yl(and 1H-pyrazol-5-yl)oxyacetamides of general formula

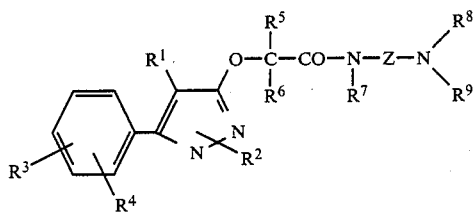

Specifically disclosed are (1)N-[2-(diethylamino)ethyl]-2-[(5-phenyl-1H-pyrazol-3-yl)oxy]acetamide, example 5, and (2) N-[3-(diethylamino)propyl]-2-[(5-phenyl-1H-pyrazol-3-yl)oxy]acetamide, example 24.

U.S. Pat. No. 4,182,895, to Bailey discloses as an intermediate in the synthesis of 1-amino-lower-alkyl-3,4-diphenyl-1H-pyrazoles "β-[1-(3,4-diphenyl-1H-pyrazolyl)]-N,N-dimethylpropionamide" at column 8, line 63 to 64.

European patent applications 248594, 293220, and 293221 to Ortho Pharmaceutical Corporation describe the synthesis of 1,5-dipenyl-1H-pyrazole-3-alkanoic acids and the use of these acids and their esters as cyclooxygenase and lipoxygenase inhibitors.

Bondavalli et al. [Farmaco, Ed. Sci 43, 725–743(1988)]disclose N-alkyl carbamates of 1-(2-hydroxyethyl)-3,5-diphenyl-1H-pyrazole as antihypertensive, antiarrytmic, analogesic, antiinflammatory and hypoglycemic agents. Specifically disclosed are the ethyl, isopropyl, phenyl and 1-naphthyl carbamates.

U.S. Pat. No. 4,072,498 to Moon and Kornis discloses N,N,α,α-tetramethyl-3,4-diphenyl-1H-pyrazole-1-acetamide as a herbicide (example 160).

Ezrin et al. [*FASEB Journal* 2, A1557(1988)], a publication from our own laboratory, describes the antiarrhythmic activity of N-[3-(diethylamino)propyl]-4,5-diphenyl-1H-pyrazole-1-acetamide fumarate.

European patent application No. 299,407, published Jan. 18, 1989, discloses an extensive series of 4,5-diaryl-1H-pyrazole-1-alkanamides as antiarrhythmic agents.

SUMMARY OF THE INVENTION

In a product aspect the invention relates to compounds of the formula Ia or Ib

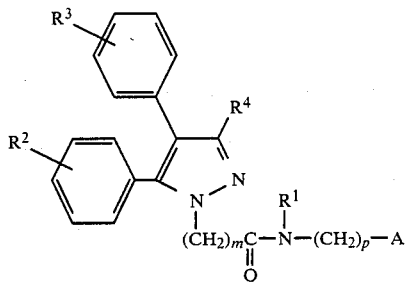

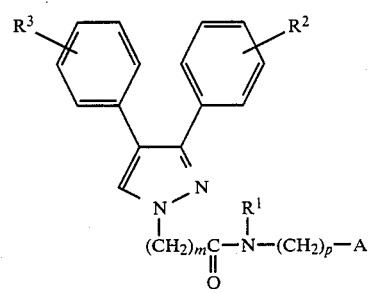

or acid-addition salt thereof wherein $R^1$ is hydrogen or lower-alkyl; $R^2$ and $R^3$ are independently hydrogen, hydroxy, lower-alkyl, lower-alkoxy, lower-alkylamino, lower-alkylamido, lower-alkylsulfonamido, nitro, amino, cyano, or halo; $R^4$ is hydrogen or hydroxy; m is one or two; p is one, two, or three; and A is a five-or six-membered heterocycle, composed of carbon and nitrogen, attached to —$(CH_2)_p$— at a carbon, and optionally substituted with a lower-alkyl group.

Lower-alkyl as used herein describes linear or branched hydrocarbon chains of four or fewer carbon atoms; lower-alkoxy as used herein describes linear or branched alkyloxy substituents containing four or fewer carbon atoms; halogen describes bromine, chlorine or fluorine.

Examples of heterocycles within the scope of the invention are pyrroidine, piperidine, piperazine, imidazole, pyrrole, pyridine, pyrimidine, pyrazine, N-methylpyrrolidine, N-ethylpyrrolidine, N-methylpiperidine, N-ethylpiperidine, N-methylpiperazine, and N-ethylpiperazine.

In a further product aspect, the invention relates to compositions for treating cardiac arrhytmia which comprise compounds of the formula I together with pharmaceutically acceptable excipients or diluents as required.

In a process aspect, the invention relates to a method for treating cardiac arrhytmia in a mammal which comprises administering to said mammal an antiarrhytmically effective amount of a compound of formula I.

Processes are described for preparing a compound of formula I which comprise reacting a pyrazole-1-acetate or propanoate ester or a pyrazole-1-acetic propanoic acid with an amine.

DETAILED DESCRIPTION INCLUSIVE OF PREFERRED EMBODIMENTS

The synthesis of compounds of the invention may be outlined as shown in scheme A wherein $R^5$ is hydrogen or lower-alkyl.

Scheme A

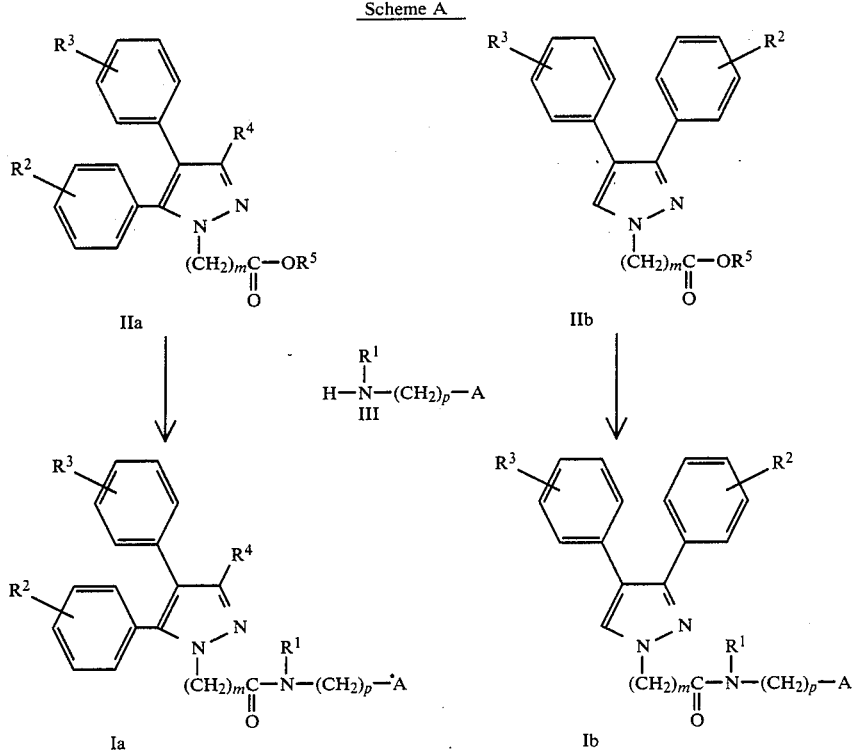

When $R^5$ is lower-alkyl, the lower-alkyl ester, preferably a methyl or ethyl ester, of a suitably substituted 3,4- or 4,5-diphenylpyrazole-1-alkanoic acid (II) is reacted with an excess of a primary or secondary amine of formula III at 20° to 150° C., preferably at 90° to 150° C. When the amine is valuable, the ester II is preferably reacted with about one equivalent of the amine III in the presence of a tertiary amine, preferably diisopropylethylamine, in an inert solvent.

Alternatively, the compounds of the invention may be synthesized from the free acids. Thus a suitably substituted 3,4- or 4,5-diphenyl-1H-pyrazole-1-acetic or propanoic acid (IIa or IIb wherein $R^5$ is hydrogen) is activated by procedures well-known in the art, such as reaction with an acid chloride to form a mixed anhydride, reaction with a carbodiimide to form an O-acylisourea, or reaction with carbonyl diimidazole to form an imidazolide. The activated acid in an inert solvent is then combined at −20° C. to 75° C. with a stoichiometric amount or a slight excess of a primary or secondary amine of formula III.

The ester IIa where $R^4$ is hydrogen and m is one, or IIb where m is one may be synthesized from the appropriately substituted desoxybenzoin by formylation by means of known procedures [Russell et al *J. Am. Chem. Soc.* 76, 5714(1954)] followed by condensation with a hydrazinoacetic acid ester in a suitable solvent, preferably ethanol, at 20° to 100° C., preferably at 25° C. The hydrazinoacetate is preferably used in the form of a mineral acid salt from which the free hydrazine may be liberated in situ by the addition of about one equivalent of a base, preferably pyridine.

Ester IIa where $R^4$ is hydrogen and m is two or IIb where m is two may be synthesized from the appropriately substituted diaryl pyrazole; by a two step procedure comprising reaction with acrylonitrile in the presence of base in an inert solvent at 0°–50° C., preferably at about 20° C., followed by hydrolysis of the nitrile using methanol and hydrogen chloride in an inert solvent at 0° to 30° C. and then water at 0°–30° C.

When only the 4,5-diphenyl isomer of the products of formula Ia where m is one and $R^4$ is hydrogen is desired, the 4,5-diphenyl ester IIa where $R^4$ is hydrogen may be synthesized from the appropriately substituted desoxybenzoin by a two-step procedure comprising reaction with N,N-dimethylformamide dimethyl acetal in an inert solvent, preferably methyl tert-butyl ether, at 20°–100° C., preferably at about 55° C., followed by cyclization with a lower-alkyl ester of hydrazinoacetic acid as described above.

Other processes for the production of ester IIa where $R^4$ is hydrogen and m is two or IIb where m is two, as well as a detailed description of the determination of the identity of particular isomers, are described in U.S. Pat. No. 4,182,895.

The ester IIa where $R^4$ is hydroxy may be synthesized from the appropriate 3,4-diphenyl-5-pyrazolone by alkylation with an ω-haloalkanoate in the presence of about one equivalent of a base, preferably potassium carbonate, in an inert solvent at 20°–100° C., preferably at about 55° C.

The compounds of formulas Ia and Ib are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts that is, salts whose anions are relatively innocuous to the animal organism in medicinal doses of the salts so that the beneficial properties inherent in the free base are not vitiated by side effects ascribable to the anions. In practicing the present invention it is convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance, and mass spectroscopy. The course of the reactions and the identity and homogeneity of the products were assessed by thin layer chromatography (TLC) or gas-liquid chromatography (GLC). The starting materials are either commercially available or may be prepared by procedures well known in the art.

In the following procedures melting points are given in degrees C and are uncorrected. The abbreviation THF stands for tetrahydrofuran, DMF stands for N,N-dimethylformamide and Ac stands for the acetyl residue, CH$_3$CO.

EXAMPLE 1A

Ethyl 4,5-diphenyl-1H-pyrazole-1-acetate

A slurry of 200 g (0.89 mol) of formyldesoxybenzoin and 138 g (0.89 mol) of ethyl hydrazinoacetate hydrochloride in 2 L of ethanol were stirred at room temperature and 72 mL (0.89 mol) of pyridine was added dropwise. The reaction was stirred at room temperature and progress was assessed by periodic TLC using 3% acetic acid, 25% acetone and 72% toluene on silica gel. When, after the addition of a further 3 mL of pyridine over the course of 18 hours, the reaction was judged completely by TLC, the solvent was stripped in vacuo and the residue slurred in ethyl acetate. The ethyl acetate solution was filtered free of solid impurity, washed with water then saturated sodium chloride solution and dried over magnesium sulfate. The ethyl acetate was stripped to a reddish oil which was triturated in pentane to yield 156 g of solid. The product was recrystallized carefully from ether-pentane to yield 44.6 g of ethyl 4,5-diphenyl-1H-pyrazole-1-acetate, mp 79°–81° C. By repeated careful crystallization from ether-pentane a further 99.6 g of the 4,5-diphenyl isomer may be obtained for a total yield of 144.2 g (53% yield).

EXAMPLE 1B

Ethyl 4,5-Diphenyl-1H-pyrazole-1-acetate

When only the 4,5-diphenyl isomer is desired the following procedure is preferred. A mixture of 778 g (3.96 mol) deoxybenzoin, 580 mL (4.38 mol) of N,N-dimethylformamide dimethyl acetal, and 775 mL of methyl tert-butyl ether was refluxed for 3 hours. The reaction mixture was cooled on ice to 0°–5° C. The precipitated solid was collected by filtration, the filter cake washed with 250 mL of cold methyl tert-butyl ether twice and dried in vacuum chamber at 65° C. to afford 913 g (92%) of 3-(dimethylamino)-1,2-diphenyl-2-propen-1-one, mp 128°–133° C. A slurry of 913 g (3.64 mol) of 3-(dimethylamino)-1,2-diphenyl-2-propen-1-one in 3.4 L of absolute ethanol was treated with 618 g (4 mol) of ethyl hydrazinoacetate hydrochloride in one portion. The mixture was stirred at room temperature for 1 hour, filtered through diatomaceous earth, and the filtrate treated with 7 L of 50% aqueous ethanol with stirring. Cooling of the resultant solution to 0°–5° C. provided a white solid which was collected by filtration, washed with 250 mL of cold 50% ethanol twice and dried in vacuum at 40° C. to provide 970 g (87%) of ethyl 4,5-diphenyl-1H-pyrazole-1-acetate, mp 76°–80° C., containing none of the 3,4-diphenyl isomer detectable by GLC.

EXAMPLE 2

Ethyl 3,4-diphenyl-1H-pyrazole-1-acetate

Chromatography of the mother liquors from Example 1A on silica gel using 1:1 chloroform-hexane provided up to 20% of the 3,4-diphenyl isomer. The 3,4-diphenyl isomer (Example 2) may be distinguished from the 4,5-diphenyl isomer (Example 1) by its higher Rf on TLC. An analytical sample may be obtained by distillation at 0.2 mm, boiling range 186°–189° C.

EXAMPLE 3

Ethyl 4,5-bis(4-fluorophenyl)-1H-pyrazole-1-acetate and ethyl 3,4-bis(4-fluorophenyl)-1H-pyrazole-1-acetate Following the procedure of Example 1, 19.7 g (0.076 mol) of 1,2-bis(4-fluorophenyl)-3-hydroxy-2-propen-1-one, 11.8 g (0.076 mol) of ethyl hydrazinoacetate hydrochloride and 6.3 mL (0.078 mol) of pyridine were reacted at room temperature to produce 19.9 g of the mixed 4,5-and 3,4-diphenyl isomers. The isomers were separated by high pressure liquid chromatography on silica gel eluting with 97% toluene, 3% ethyl acetate. The peak with k'=2.0 yielded 1.8 g of the 3,4-diphenyl isomer, mp 98°–99° C., and the peak with k'=4.0 yielded 11.16 g of the 4,5-diphenyl isomer, mp 83°–84° C.

EXAMPLE 4

Methyl 3,4-diphenyl-1H-pyrazole-1-propanoate and Methyl 4,5-diphenyl-1H-pyrazole-1-propanoate Thirty grams (0.136 mol) of 3,4(4,5)-diphenylpyrazole and 11.2 mL (0.169 mol) of acrylonitrile were combined in 450 mL of methylene dichloride and 0.56 g (0.01 mol) of sodium methoxide were added. The mixture was heated with stirring under nitrogen for four hours and allowed to stand under nitrogen for 18 hours. The reaction was filtered and evaporated under vacuum below 30° C. The residue was taken up in hot absolute alcohol and cooled. The first crop of 22.7 g of damp solid was shown by NMR to consist of 30° of the 3,4 isomer and 70° of the 4,5 isomer. It was recrystallized a second time from about 350 mL of ethanol to yield 11 g of the pure 4,5 diphenyl isomer, mp 123°–124° C. A second crop of 9 g of damp solid from the first crystalization was shown by NMR to be essentially pure 3,4 diphenyl isomer mp 82°–85° C.

In an ice bath under nitrogen, hydrogen chloride gas was passed through a suspension of 100 mg (0.4 mol) of 4,5 diphenyl pyrazole-1-propionitrile and 2 mL of dry methanol for 5 to 10 minutes. Since the starting nitrile was not in solution, 2 mL of THF and 2 mL of methanol were added. The mixture was again treated with hydrogen chloride gas. The temperature shot above 20° C. and the hydrogen chloride gas was turned off. The reaction was stirred at room temperature for 48 hours, and 70 mg of crystalline iminoether hydrochloride was filtered off, mp 90°–91° C.

The iminoether hydrochloride was dissolved in 5 mL of methylene chloride, cooled to 0° C., and 10 drops of water were added. The reaction was stirred for a few minutes at 0° C. and then for a few minutes at room temperature. The methylene chloride layer was separated and dried over magnesium sulfate, filtered and evaporated to yield 30 mg of methyl 4,5-diphenyl-1H-pyrazole-1-propanoate, mp 72°–74° C.

EXAMPLE 5

Ethyl 4-(4-methoxyphenyl)-5-phenyl-1H-pyrazole-1-acetate

Following the procedure of example 1B 11 g (0.39 mol) of 3-(dimethylamino)-2-(4-methoxyphenyl)-1-phenyl-2-propene-1-one and 6.6 g (0.43 mol) of ethyl hydrazinoacetate hydrochloride were reacted in 55 mL of absolute methanol under nitrogen. After 1½ hours, 11.2 g of solid product was filtered off, mp 81°–84° C.

EXAMPLE 6

Ethyl 5-(4-hydroxyphenyl)-4-phenyl-1H-pyrazole-1-acetate

Following the procedure of example 1B, 15 g (0.05 mol) of 3-(dimethylamino)-1-(4-hydroxyphenyl)-2-phenyl-2-propene-1-one and 9 g (0.058 mol) of ethyl hydrazino acetate hydrochloride were reacted in 75 mL of absolute ethanol. After 1½ hours, 14.38 g of solid product was filtered off, mp 130°–135° C.

EXAMPLE 7

Ethyl 4-(4-fluorophenyl)-5-phenyl-1H-pyrazole-1-acetate

Following the procedure of example 1B, 13.8 g (0.0645 mol) of 2-(4-fluorophenyl)-1-phenylethanone was reacted with 20 mL of dimethyl formamide dimethyl acetal to yield 13.6 g of 3-(dimethylamino)-2-(4-fluorophenyl)-1-phenyl-2-propen-1-one, mp 115°–116° from isopropyl acetate. The enamine (10.5 g, 0.039 mol) was reacted with 6.03 g (0 039 mol) of ethyl hydrazinoacetate hydrochloride to yield 12.1 g of product mp 86°–87° C. from methyl-t-butyl ether.

EXAMPLE 8

Ethyl 4-(4-nitrophenyl)-5-phenyl-1H-pyrazole-1-acetate

By a procedure analogous to that of example 7, 11.9 g of ethyl 4-(4-nitrophenyl)-5-phenyl-1H-pyrazole-1-acetate, mp 78–79 from methyl t-butyl ether, was synthesized from 17.6 g (0.073 mol) of 2-(4-nitrophenyl)-1-phenylethanone, 35 mL of dimethyl formamide dimethyl acetal and 7.04 g (0.0456 mol) of ethyl hydrazinoacetate hydrochloride.

EXAMPLE 9

Ethyl 4-(4-chlorophenyl)-5-phenyl-1H-pyrazole-1-acetate

By a procedure analogous to that of example 7, 8.5 g of ethyl 4-(4-chlorophenyl)-5-phenyl-1H-pyrazole-1-acetate mp 75°–76° from triethylamine, was synthesized from 11.48 g (0.049 mol) of 2-(4-chlorophenyl)-1-phenylethanone, 12 mL of dimethyl formamide dimethyl acetal and 4.95 g (0.032 mol) of ethyl hydrazinoacetate hydrochloride.

EXAMPLE 10

Ethyl 4-(4-cyanophenyl)-5-phenyl-1H-pyrazole-1-acetate

By a procedure analogous to that of example 7, 6.7 g of ethyl 4-(4-cyanophenyl)-5-phenyl-1H-pyrazole-1-acetate, mp 124°–125° from methyl t-butyl ether, was synthesized from 7.72 g (0 035 mol) of 2-(4-cyanophenyl)-1-phenylethanone, 10 mL of dimethyl formamide dimethyl acetal and 3.7 g (0.024 mol) of ethyl hydrazino-acetate hydrochloride.

The 2-(4-cyanophenyl)-1-phenylethanone was synthesized from 4-cyanobenzyl bromide and -cyano-N,N-diethylbenzenemethanamine: 3.95 g (0.16 mol) of sodium hydride was suspended in 80 mL of DMF under nitrogen and 29.9 g (0.16 mol) of the methanamine in 20 mL of DMF was added dropwise. When evolution of hydrogen had ceased, 31.2 g (0.16 mol) of the benzyl bromide in 30 mL of toluene was added and the reaction stirred 3 hr at room temperature. The reaction was stripped, 300 mL of 6N HCL was added and the suspension was stirred 4 hr, let sit 18 hr and extracted with chloroform. The chloroform extract was stripped, dissolved in ethyl acetate, and filtered through silica gel to remove a purple impurity. The ethyl acetate solution was stripped, the residue was triturated in ether and recrystallized from methanol to give 7.72 g of 2-(4-cyanophenyl)-1-phenylethanone, mp 113°–114° C.

EXAMPLE 11

Ethyl 5-[4-(dimethylamino)phenyl]-4-phenyl-1H-pyrazole-1-acetate

By a procedure analogous to that of example 7, 13.7 g of ethyl 5-[4-(dimethylamino)phenyl]-4-phenyl-1H-pyrazole-1-acetate, mp 99°–101° C. from ether, was synthesized from 13.0 g (0.054 mol) of 1-[4-(dimethylamino)phenyl]-2-phenylethanone, 27.6 mL (0.196 mol) of dimethyl formamide dimethyl acetal and 7.9 g (0.05 mol) of ethyl hydrazinoacetate hydrochloride.

EXAMPLE 12

4,5-diphenyl-1H-pyrazole-1-acetic acid

Twelve grams (0.04 mol) of ethyl 4,5-diphenyl-1-H-pyrazole-1-acetate of example 1 was refluxed in 40 mL of water, 40 mL of ethanol and 5 mL of 35% aqueous sodium hydroxide for 1.5 hours. The ethanol was stripped off, water was added, and the slurry was acidified with excess 6N HCl. The resulting precipitate was filtered off and rinsed with water to yield 10.4 g of free acid, mp 169°–170° C.

EXAMPLE 13

4,5-Diphenyl-N-[2-(1-piperidinyl)ethyl]-1H-pyrazole-1-acetamide

A mixture of 15 g (0.049 mol) of ethyl 4,5-diphenyl-1H-pyrazole-1-acetate of example 1 and 10.2 mL (0.072 mol) of N-(2-aminoethyl)piperidine in 62 ml of diisopropylethylamine was stirred at 100° C. for 18 hr. Upon cooling and standing a solid precipitate was formed which was filtered off and recyrtallized very slowly from 250 mL of 1:3 THF-ether to yield 10.6 of 4,5-Diphenyl-N-[2-(1-piperidinyl)ethyl]-1H-pyrazole-1-acetamide mp 95°–97° C.

EXAMPLE 14

4,5-Diphenyl-N-[3-(1-pyrrolidinyl)propyl]-1H-pyrazole-1-acetamide

A mixture of 15 g (0.049 mol) of ethyl 4,5-diphenyl-1H-pyrazole-1-acetate and 60 mL of N-(3-aminopropyl) pyrrolidine was stirred at 100° C. for 48 hr. The excess aminopropylpyrrolidine was stripped in vacuo and the residue was triturated in ether to yield 5.5 g of product mp 75°–79° C.

EXAMPLE 15

4,5-Diphenyl-N-[2-(1-pyrrolidinyl)ethyl]-1H-pyrazole-1-acetamide

By a procedure substantially similar to that of Example 13, 6.67 g of 4.5-diphenyl-N-2-(1-pyrrolidinyl)ethyl-]1H-pyrazole-1-acetamide, mp 80°–84° C., was prepared from 15 g (0.049 mol) of ethyl 4,5-diphenyl-1H-pyrazole-1-acetate of Example 1, 9 mL (0.072 mol) of N-(2-aminoethyl)pyrrolidine and 62 mL (0.36 mol) of diisopropylethylamine.

EXAMPLE 16

4,5-Diphenyl-N-[3-(1-piperidinyl)propyl]-1H-pyrazole-1-acetamide hemihydrate

A mixture of 15 g (0.049 mol) of ethyl 4,5-diphenyl-1H-pyrazole-1-acetate of Example 1, 10.2 g (0.02 mol) of 3-aminopropylpiperidine, and 62 mL of diisopropylethylamine was stirred on a steam bath under nitrogen for 18 hours. The excess amine was stripped in vacuo. The residue was taken up in about 300 mL of ether and washed twice with water. The product was extracted into 150 mL of cold water containing 18 mL of 10% hydrochloric acid. The water layer was washed two times with ether, treated with decolorizing carbon, filtered, chilled and made basic with solid sodium carbonate. The product was extracted into methylene dichloride, dried over sodium sulfate, filtered, and stripped to 14.7 g of solid residue. The residue was triturated in water, filtered and dried to yield 12.36 g of 4,5-diphenyl-N-[3-(1-piperidinyl)propyl]-lH-pyrazole-1-acetamide hemihydrate, mp 81°–85° C.

EXAMPLE 17

3,4-Diphenyl-N-[2-(1-piperidinyl)ethyl-]-1H-pyrazole-1-acetamide

By a procedure substantially similar to that of Example 13, 14.0 g of 3,4-diphenyl-N-[2-(1-piperidinyl)ethyl]1H-pyrazole-1-acetamide was prepared from 16.4 g (0.054 mol) of ethyl 3,4-diphenyl-1H-pyrazole-1-acetate, 10 g (0.07 mol) of 2-aminoethylpiperidine, and 65 mL (0.37 mol) of diisopropylethylamine. The product was not recrystallized but was triturated in ether, mp 120°–124° C. A second polymorph of mp 142°–144° C. may be obtained by recrystallizing from ethyl acetate.

EXAMPLE 18

3,4-Diphenyl-N-[3-(1-piperidinyl)propyl]-1H-pyrazole-1-acetamide (E)2-butenedioate (1:1)

A mixture of 20 g (0.065 mol) of ethyl 3,4-diphenyl-1H-pyrazole-1-acetate of Example 2, 13.7 g (0.096 mol) of N-(3-aminopropyl)piperidine, and 78 mL of diisopropylethylamine was stirred on a steam bath under nitrogen for 18 hours. The reaction was stripped to dryness, the residue dissolved in dichloromethane, washed twice with water and once with saturated sodium chloride solution. The product was extracted into about 100 mL of cold water containing about 12 mL of 10% HCl. The water layer was made basic with solid sodium carbonate and the product extracted into methylene dichloride, dried over sodium sulfate and stripped. The product was purified by chromatography on silica gel eluting with 5% triethylamine in chloroform. The purified product was crystallized from acetone as the fumarate salt and was recrystallized from ethanol to yield 8.56 of product, mp 179°–180° C.

EXAMPLE 19

N-[2-(1-Methyl-2-pyrrolidinyl)ethyl]-4,5-diphenyl-1H-pyrazole-1-acetamide (E) 2-butenedioate (1:1) hemihydrate A sodium of 10 g (0.033 mol) of ethyl 4,5-diphenyl-1H-pyrazole-1-acetate of example 1 in 9.6 mL (0 066 mol) of 2-(2-aminoethyl)-1-methylpyrrolidine was stirred at 100° C. for 18 hr. The reaction was dissolved in methylene chloride, washed several times with water, dried over magnesium sulfate, and stripped to a brownish-yellow oil. The oil was dissolved in ethanol, 1 equivalent of fumaric acid was added, and the solution was stripped in vacuo. The resulting foam was crystallized from acetonitrile-ether to yield 10.6 g of product. mp 109°–110° C.

EXAMPLE 20

N-[2-(1H-imidazol-4-yl)ethyl]-4,5-diphenyl-1H-pyrazole-1-acetamide (4:1) hydrate A solution of 5.5 g (0.02 mol) of 4.5-diphenyl-1H-pyrazole-1-acetic acid of example 12 and 3.6 g (0.022 mol) of carbonyldiimidazole in 150 mL of dioxane was refluxed 2 hr and cooled to about 10° C. 3.7 g (0.02 mol) of histamine dihydrochloride and 5.7 mL (0.04 mol) of triethylamine were added and the suspension was stirred at room temperature 18 hr. TLC (10% methanol in ether on silica gel) showed incomplete reaction, so the mixture was heated at 75° C. for a further 2.5 hr. The suspension was cooled, filtered, the filtrate stripped to about 95 mL volume, and chilled. The resulting needles were filtered off and rinsed with a very small amount of water to yield 3.8 g of product, mp 198°–199.5° C.

EXAMPLE 21

N-Methyl-N-[2-(1-piperdinyl)ethyl]-4,5-diphenyl-1H-pyrazole-1-propanamide

By process substantially similar to that of example 19 it is contemplated that N-methyl-N-[2-(1-piperidinyl)ethyl]-4,5-diphenyl-1H-pyrazole-1-propanamide may be synthesized from methyl 4,5-diphenyl-1H-pyrazole-1- propanoate of example 4 and 1-[2-(methylamino)ethyl]-piperidine.

EXAMPLE 22

4-(4-Chlorophenyl)-N-[(1-methyl-3-piperidinyl)methyl]-5-phenyl-1H-pyrazole-1-acetamide By a process substantially similar to that of example 19 it is contemplated that 4-(4-chlorophenyl)-N-[(1-methyl-3-piperidinyl)methyl]-5-phenyl-1H-pyrazole-1-acetamide may be synthesized from ethyl 4-(4-chlorophenyl)-5-phenyl-1H-pyrazole-1-acetate of example 9 and 1-methyl-3-piperidinemethanamine.

EXAMPLE 23

5-[4-(Dimethylamino)phenyl]-4-phenyl-N-[(3-pyridinyl)methyl]-1H-pyrazole-1-acetamide By a process substantially similar to that of example 19 it is contemplated that 5-[4-(dimethylamino)phenyl]-4-phenyl-N-[(3-pyridinyl)methyl]-1H-pyrazole-1-acetamide may be synthesized from ethyl 5-[4-(dimethylamino)phenyl]-4-phenyl-1H-pyrazole-1-acetate of example 11 and 3-(aminomethyl)pyridine.

EXAMPLE 24

Ethyl 3-hydroxy-4,5-diphenyl-1H-pyrazole-1-acetate or Ethyl 1,2-dihydro-3-oxo-4,5-diphenyl-3H-pyrazole-1-acetate A suspension of 3.3 mL (0.03 mol) of ethyl bromoacetate, 3.9 g (0.028 mol) of anhydrous, milled potassium carbonate and 6.7 g (0.028 mol) of 1,2-dihydro-4,5-diphenyl-2H-pyrazol-3-one obtained by the method of Gruenanger and Finzi [Chemical Abstracts 58:516f (1963)] in 67 mL of acetone was stirred at reflux for 24 hours. The solvent was removed in vacuo and the residue was chromatographed on a 45×300 mm silica gel column eluting with a gradient from 0 to 10% ethyl acetate in hexane, taking 75 mL fractions. Fractions 50-65 contained in the O-alkylated product; fractions 75-79 provided 1.1 g of the desired N-alkylated product, mp 181°-183° C.

EXAMPLE 25

N-(1-Ethyl-4-piperidinyl)-3-hydroxy-4,5-diphenyl-1H-pyrazole-1-acetamide

By a process substantially similar to that of example 19 it is contemplated that N-(1-ethyl-4-piperidinyl)-3-hydroxy-4,5-diphenyl 1H-pyrazole-1-acetamide may be synthesized from ethyl 3-hydroxy-4,5-diphenyl-1H-pyrazole-1-acetate of example 25 and 1-ethyl-4-piperidinamine.

Other examples of (heterocycle)alkyl-substituted pyrazole-1-alkanamides can be synthesized utilizing procedures analogous to the foregoing. Many compounds which could be utilized as starting materials as described in copending U.S. application D.N. 7398C of Denis M. Bailey which is incorporated herein by reference.

The antiarrhythmic activity of compounds of the invention was demonstrated by the following procedure.

Duncan Hartley guinea pigs (600-900 grams) of either sex were anesthetized with urethane (1.4 g/kg, i.p.) and supplemented as needed. An intravenous route for drug administration was established using microbore tubing inserted into the jugular vein. The induction of arrhythmias by aconitine hydrochloride (34 g/kg) was evaluated in control guinea pigs given 1 cc saline as an intravenous bolus 10 minutes prior to aconitine challenge.

Compounds to be tested were administered intravenously 10 minutes prior to aconitine challenge at an initial dosage of 30 mg/kg. This dosage was reduced in subsequent animals if severe cardiac rhythm disturbances persisted beyond two minutes after injection in the first guinea pig tested. All drugs were tested at the maximally tolerated dose (identified by the lack of arrhythmias in the EKG prior to aconitine challenge). Compounds were administered in saline as 1 cc bolus injections (n=5-9).

Time intervals between aconitine injection and the appearance of arrhythmias were determined. Specifically noted was the time until the onset of (i) the first premature ventricular contraction (PVC); (ii) the first sustained run of ventricular tachycardcia consisting of 10 or more ventricular beats (VTACH); and (iii) the time until the appearance of ventricular fibrillation lasting longer than 15 seconds (VFIB). The average time and standard error of the mean until the appearance of these arrhythmias were calculated for each treatment group and compared to concurrent controls using a one-way analysis of variance. Activity was defined as a statistically significant delay in the onset of PVC, VTACH and VFIB time course compared to control values.

The following table summarizes the results obtained from the testing of representative compounds of the invention.

| Example No. | Minutes to | | |
| --- | --- | --- | --- |
| | PVC | VTACH | VFIB |
| Control | 1.0-1.9 | 1.4-2.5 | 3.1-4.3 |
| 13 | 7.9 | 10.7 | 35.4 |
| 14 | 5.1 | 6.3 | 25.7 |
| 15 | 2.9 | 3.0 | 15.5 |
| 16 | 5.2 | 15.4 | 27.6 |
| 17 | 3.6 | 9.6 | 30.0 |
| 18 | 3.6 | 8.0 | 29.0 |
| 19 | 16.8 | 20.9 | 34.4 |
| 20 | 6.3 | 9.3 | 29.0 |

The compounds of the invention can be prepared for use by conventional pharmaceutical procedures: that is, by dissolving or suspending them or their pharmaceutically acceptable salts in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

The percentage of active component in the composition and method for treating or preventing arrhythmia can be varied so that a suitable dosage is obtained. The dosage administered to a particular patient is variable depending upon the clinician's judgement using as the criteria: the route of administration, the duration of treatment, the size and condition of the patient, the potency of the active component, and the patient's response thereto. An effective dosage amount of active component can thus be determined by the clinician considering all criteria and utilizing his best judgement on the patient's behalf.

We claim:

1. A compound of formula

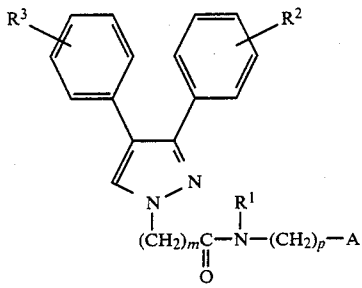

or

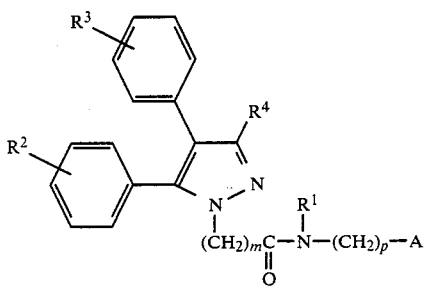

or acid-addition salt thereof wherein $R^1$ is hydrogen or lower-alkyl; $R^2$ and $R^3$ are independently hydrogen, hydroxy, lower-alkyl, lower-alkoxy, lower-alkylamino, lower-alkylamido, lower-alkylsufonamido, nitro, amino, cyano, or halo; $R^4$ is hydrogen or hydroxy; m is one or two; p is one, two, or three; and A is a five-or six membered heterocycle containing carbon, hydrogen and nitrogen and attached to $(CH_2)_p$ at a carbon, or A is a five-or six-membered heterocycle, substituted with a lower-alkyl group, containing carbon, hydrogen and nitrogen and attached to $(CH_2)_p$ at a carbon.

2. A compound according to claim 1 wherein m is one.

3. A compound according to claim 2 wherein $R^4$ is hydrogen and having the formula.

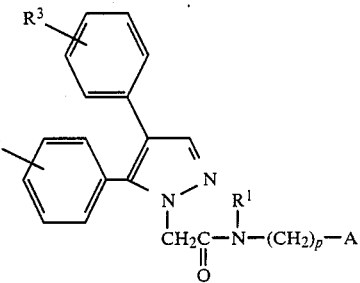

4. A compound according to claim 3 wherein p is two.

5. A compound according to claim 4 wherein A is an imidazole.

6. N-[2-(1H-imidazol-4-yl)ethyl]-4,5-diphenyl-1H-pyrazole-1-acetamide or a salt or solvate thereof according to claim 5.

7. A compound according to claim 6 wherein A is a lower-alkyl-substituted pyrrolidine.

8. N-[2-(1-methyl-2-pyrrolidinyl)ethyl]-4,5-diphenyl-1H-pyrazole-1-acetamide or a salt or solvate thereof according to claim 7.

9. A composition for treating cardiac arrhythmias comprising an amount of a compound according to claim 1 effective to treat cardiac arrhythmias together with one or more pharmaceutically acceptable excipients or diluents.

10. A composition for treating cardiac arrhythmias comprising an amount of a compound according to claim 3 effective to treat cardiac arrhythmias together with one or more pharmaceutically acceptable excipients or diluents.

11. A composition for treating cardiac arrhythmias comprising an amount of a compound according to claim 4 effective to treat cardiac arrhythmias together with one or more pharmaceutically acceptable excipients or diluents.

12. A composition for treating cardiac arrhythmias comprising an amount of N-[2-(1-methyl-2-pyrrolidinyl)ethyl]-4,5-diphenyl-1H-pyrazole-1-acetamide or pharmaceutically acceptable acid addition salt or solvate thereof according to claim 8 effective to treat cardiac arrhythmias together with one or more pharmaceutically acceptable excipients or diluents.

13. A method for treating cardiac arrhythimas in a susceptible subject which comprises the step of administering an amount of a compound according to claim 1 effective to treat cardiac arrhythmias.

14. A method for treating cardiac arrhythmias in a susceptible subject which comprises the step of administering an amount of a compound according to claim 3 effective to treat cardiac arrhythmias.

15. A method for treating cardiac arrhythmias in a susceptible subject which comprises the step of administering an amount of a compound according to claim 4 effective to treat cardiac arrhythmias.

16. A method for treating cardiac arrhythmias in a susceptible subject which comprises the step of administering an amount of 2-(1-methyl-2-pyrrolidinyl)ethyl]-4,5-diphenyl-1H-pyrazole-1-acetamide or pharmaceutically acceptable acid addition salt thereof according to claim 8 effective to treat cardiac arrhythmias.

* * * * *

UNITED STATES PATENT AND TRADEMARK OFFICE
CERTIFICATE OF CORRECTION

PATENT NO. : 4,898,880

DATED : February 6, 1990

INVENTOR(S) : Denis M. Bailey, George Y. Lesher, Thomas E. D'Ambra

It is certified that error appears in the above-identified patent and that said Letters Patent is hereby corrected as shown below: On the Title page, item [54] and col. 1, line 1, Title: "N-(Heterocycle)Alkyl)" should read --- N-[(Heterocycle)Alkyl] ---.

Column 1, line 44: "dipenyl" should read --- diphenyl ---.

Column 1, line 50: "antiarrhytmic" should read --- antiarrhythmic ---.

Column 1, line 50: "analogesic" should read --- analgesic ---.

Column 2, line 44: "pyrroidine" should read --- pyrrolidine ---.

Column 2, line 50: "arrhytmia" should read --- arrhythmia ---.

Column 2, line 55: "arrhytmia" should read --- arrhythmia ---.

Column 2, line 56 "antiarrhytmically" should read --- antiarrhythmically ---.

Column 3, line 66: "pyrazole; by" should read --- pyrazole by ---.

Column 5, line 51: "slurred" should read --- slurried ---.

Column 9, line 30: "4.5-diphenyl" should read --- 4,5-diphenyl ---.

Column 10, line 31: "sodium" should read --- solution ---.

Column 11, line 39: "contained in the" should read --- contained the ---.

Column 11, line 48: "diphenyl 1H" should read --- diphenyl-1H ---.

Column 11, line 55: "as described" should read --- are described ---.

UNITED STATES PATENT AND TRADEMARK OFFICE
CERTIFICATE OF CORRECTION

PATENT NO. : 4,898,880

DATED : February 6, 1990

INVENTOR(S) : Denis M. Bailey, George Y. Lesher, Thomas E. D'Ambra

It is certified that error appears in the above-identified patent and that said Letters Patent is hereby corrected as shown below:

Column 12, line 17: "tachycardcia" should read --- tachycardia ---.

Column 1, line 19: "antiarrythmic" should read --- antiarrhythmic ---.

Column 7, line 54: "0 039" should read --- 0.039 ---.

Column 8, line 21: "0 035" should read --- 0.035 ---.

Column 8, line 24: "hydrazino-acetate" should read --- hydrazinoacetate ---.

Column 9, line 10: "recyrtallized" should read --- recrystallized ---.

Column 9, line 30: "ethyl-]" should read --- ethyl]- ---.

Column 10, line 32: "0 066" should read --- 0.066 ---.

Column 10, line 40: "product." should read --- product, ---.

Column 10, line 46: "4.5" should read --- 4,5 ---.

Column 11, line 50: "example 25" should read --- example 24 ---.

Column 14, line 22: "claim 6" should read --- claim 4 ---.

Signed and Sealed this

Ninth Day of November, 1993

Attest:

BRUCE LEHMAN

Attesting Officer

Commissioner of Patents and Trademarks